United States Patent
Hegde et al.

(10) Patent No.: US 12,300,364 B2
(45) Date of Patent: May 13, 2025

(54) SYSTEMS AND METHODS OF INTEGRATED PLATFORMS FOR DYNAMIC ELECTRONIC TRANSACTIONS OF PETCARE DATA

(71) Applicant: Mars, Incorporated, McLean, VA (US)

(72) Inventors: Santosh Hegde, San Jose, CA (US);
Leonid Sudakov, New York, NY (US);
Kelvin Kwong, San Francisco, CA (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 18/319,643

(22) Filed: May 18, 2023

(65) Prior Publication Data

US 2023/0402141 A1 Dec. 14, 2023

Related U.S. Application Data

(60) Provisional application No. 63/366,181, filed on Jun. 10, 2022.

(51) Int. Cl.
*G16H 40/20* (2018.01)
*A01K 29/00* (2006.01)
(Continued)

(52) U.S. Cl.
CPC ........... *G16H 10/60* (2018.01); *A01K 29/005* (2013.01); *A61B 5/1118* (2013.01);
(Continued)

(58) Field of Classification Search
CPC .... G16H 10/60; A01K 29/005; A61B 5/1118; A61B 5/6802; A61B 5/6822; A61B 2503/40; G06Q 30/0271; G06Q 30/0277
See application file for complete search history.

(56) References Cited

U.S. PATENT DOCUMENTS 10,772,287 B1 * 9/2020 Van Eeden ............ A01K 1/033
2016/0063188 A1 3/2016 Thornberry et al.
(Continued)

FOREIGN PATENT DOCUMENTS

WO 2021253004 A1 12/2021

OTHER PUBLICATIONS

International Search Report issued in International Application No. PCT/US2023/022659 dated Jul. 14, 2023 (13 pages).
(Continued)

*Primary Examiner* — Maroun P Kanaan
(74) *Attorney, Agent, or Firm* — Bookoff McAndrews, PLLC

(57) ABSTRACT

A computer-implemented method for dynamically managing electronic transactions of petcare data is disclosed. The method includes hosting a user portal corresponding to at least one user and at least one pet, the user portal including at least one user profile and at least one pet profile, receiving a first data set from a first external system, in response to the receiving, calling a content management component using an API based on the first data set, in response to the calling, receiving a recommendation from the content management component, the recommendation based on the first data set, based on the receiving, updating one or more database records corresponding to the at least one user identifier and the at least one pet identifier, the updating based on the first data set and the recommendation, and displaying, by the one or more processors, the recommendation on a user interface of the user portal.

20 Claims, 7 Drawing Sheets

(51) Int. Cl.
*A61B 5/00* (2006.01)
*A61B 5/11* (2006.01)
*G06Q 30/0241* (2023.01)
*G06Q 30/0251* (2023.01)
*G16H 10/60* (2018.01)

(52) U.S. Cl.
CPC ....... *A61B 5/6802* (2013.01); *G06Q 30/0271* (2013.01); *G06Q 30/0277* (2013.01); *A61B 5/6822* (2013.01); *A61B 2503/40* (2013.01)

(56) References Cited

U.S. PATENT DOCUMENTS

| | | | |
|---|---|---|---|
| 2020/0068853 A1* | 3/2020 | Radovcic | H04M 1/72403 |
| 2020/0175611 A1 | 6/2020 | Gelfand | |
| 2020/0227160 A1* | 7/2020 | Youngblood | G16H 40/67 |
| 2020/0267936 A1* | 8/2020 | Tran | A01K 29/005 |

OTHER PUBLICATIONS

International Search Report issued in International Application No. PCT/US2023/020795 dated Aug. 17, 2023 (11 pages).

\* cited by examiner

SYSTEMS AND METHODS OF INTEGRATED PLATFORMS FOR DYNAMIC ELECTRONIC TRANSACTIONS OF PETCARE DATA

CROSS-REFERENCE TO RELATED APPLICATION(S)

This application claims the benefit of priority from U.S. Provisional Application No. 63/366,181, filed on Jun. 10, 2022, which is incorporated by reference herein in its entirety.

TECHNICAL FIELD

Various embodiments of this disclosure relate generally to systems and methods of integrated platforms for dynamic electronic transactions of petcare data.

BACKGROUND

A pet owner has an extreme burden regarding creating, managing, and tracking all the different types of pet data. Current solutions are generic, inefficient, and are not specifically tailored towards a pet owner's needs. Moreover, current solutions do not take into account that the pet owner may have more than one pet. Further, conventional techniques fail to provide a single personalized destination for the data management needs of a pet owner and the pet owner's pets.

This disclosure is directed to addressing above-referenced challenges. The background description provided herein is for the purpose of generally presenting the context of the disclosure. Unless otherwise indicated herein, the materials described in this section are not admitted to be prior art, or suggestions of the prior art, by inclusion in this section.

SUMMARY OF THE DISCLOSURE

According to certain aspects of the disclosure, methods and systems are disclosed for dynamically managing electronic transaction petcare data.

In one aspect, an exemplary embodiment of a computer-implemented method for dynamically managing electronic transactions of petcare data is disclosed. The method may include hosting, by one or more processors, a user portal corresponding to at least one user and at least one pet, the user portal including at least one user profile and at least one pet profile. The method may further include receiving, by the one or more processors, a first data set from a first external system, the first external system including at least one of: a wellness system, a diagnostic system, a homing system, a genetics system, or a third party services system, wherein the first data set includes at least one user identifier and at least one pet identifier. The method may further include, in response to the receiving, calling, by the one or more processors, a content management component using an application programming interface (API) based on the first data set. The method may further include, in response to the calling, receiving, by the one or more processors, a recommendation from the content management component, the recommendation based on the first data set. The method may further include, based on the receiving, updating, by the one or more processors, one or more database records corresponding to the at least one user identifier and/or the at least one pet identifier, the updating based on the first data set and the recommendation. The method may further include displaying, by the one or more processors, the recommendation on a user interface of the user portal.

In a further aspect, an exemplary embodiment of a computer system for dynamically managing electronic transactions of petcare data is disclosed, the computer system comprising at least one memory storing instructions, and at least one processor configured to execute the instructions to perform operations. The operations may include hosting a user portal corresponding to at least one user and at least one pet, the user portal including at least one user profile and at least one pet profile. The operations may further include receiving a first data set from a first external system, the first external system including at least one of: a wellness system, a diagnostic system, a homing system, a genetics system, or a third party services system, wherein the first data set includes at least one user identifier and at least one pet identifier. The operations may further include, in response to the receiving, calling a content management component using an application programming interface (API) based on the first data set. The operations may further include, in response to the calling, receiving a recommendation from the content management component, the recommendation based on the first data set. The operations may further include, based on the receiving, updating one or more database records corresponding to the at least one user identifier and/or the at least one pet identifier, the updating based on the first data set and the recommendation. The operations may further include displaying the recommendation on a user interface of the user portal.

In a further aspect, an exemplary embodiment of a non-transitory computer-readable medium storing instructions that, when executed by at least one processor, cause the at least one processor to perform operations for dynamically managing electronic transactions of petcare data is disclosed. The operations may include hosting a user portal corresponding to at least one user and at least one pet, the user portal including at least one user profile and at least one pet profile. The operations may further include receiving a first data set from a first external system, the first external system including at least one of: a wellness system, a diagnostic system, a homing system, a genetics system, or a third party services system, wherein the first data set includes at least one user identifier and at least one pet identifier. The operations may further include, in response to the receiving, calling a content management component using an application programming interface (API) based on the first data set. The operations may further include, in response to the calling, receiving a recommendation from the content management component, the recommendation based on the first data set. The operations may further include, based on the receiving, updating one or more database records corresponding to the at least one user identifier and/or the at least one pet identifier, the updating based on the first data set and the recommendation. The operations may further include displaying the recommendation on a user interface of the user portal.

It is to be understood that both the foregoing general description and the following detailed description are exemplary and explanatory only and are not restrictive of the disclosed embodiments.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
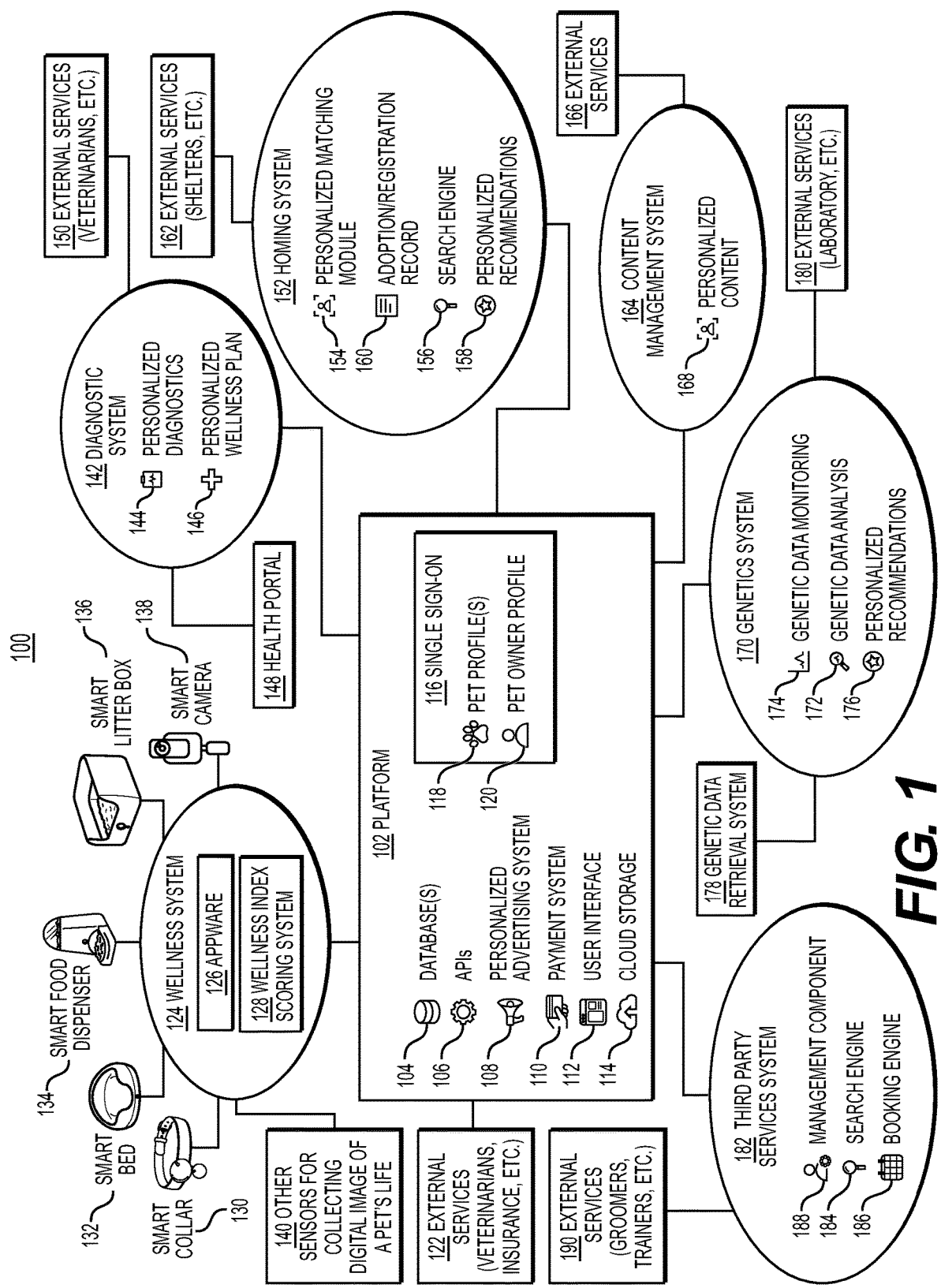
FIG. 1 depicts an exemplary platform environment, according to one or more embodiments.

According to certain aspects of the disclosure, methods and systems are disclosed for an integrated electronic pet platform. Conventional techniques may not be suitable because conventional techniques may rely on a pet owner to manually track all of the pet's data. Such techniques may involve incompatible platforms, many user names and password combinations, and may also involve the pet owner misplacing the contents of the pet's data. Additionally, conventional techniques may not dynamically adapt to the number of pets that belong to the pet owner.

The pet ownership process may involve the creation, management, and storage of a large amount of pet data. A pet owner may begin to acquire pet data during the pet search process. Throughout the lifetime of the pet, the pet owner will continue to accrue important pet data, such as vaccination records, pet activity data, analysis of the pet's genetic data, and the like. However, most sources of the pet data are independent of each other, which leads to multiple usernames and passwords, having to remember the addresses of the different sources, as well as misplacing the pet data.

A need exists for an integrated hardware, software, and diagnostic solution for virtualizing a pet's information, as well as providing a centralized repository. Such a solution allows for the tracking of pet owners and pets, an efficient transfer of pet data from a collection point to external providers, personalization, pet diagnostics, and the ability to scale the pet data collection depending on how many pets belong to a pet owner.

As will be discussed in more detail below, in various embodiments, systems and methods are described for dynamically managing electronic transactions of petcare data. The systems and methods may be able to receive a data set from an external system. The systems and methods may then call a content management component using an application programming interface (API) based on the data set. The systems and methods may then receive a recommendation from the content management component, where the recommendation is based on the data set. The systems and methods may then update one or more database records based on the data set and recommendation. The systems and methods may then display the recommendation on a user interface.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, a term such as "user" or the like generally encompasses a future pet owner, future pet owners, pet owner, and/or pet owners. A term such as "pet" or the like generally encompasses a domestic animal, such as a domestic canine, feline, rabbit, ferret, horse, cow, or the like. In exemplary embodiments, "pet" may refer to a canine.

Exemplary Platform Environment

FIG. 1 depicts an exemplary platform environment 100 that may be utilized with the techniques presented herein. More specifically, environment 100 may provide an integrated hardware and software platform for improving pet digitalization by centralizing the pet's information.

Platform 102 may communicate with one or more external systems that may collect, manage, and store different types of pet data and/or pet owner data. Platform 102 may retrieve the pet data and/or pet owner data from the one or more external systems via APIs 106. In some embodiments, platform 102 may store the pet data and/or the pet owner data. For example, platform 102 may store the pet data in pet profile(s) 118. Additionally, for example, platform 102 may store the pet owner data in a pet owner profile 120. The one or more external systems may include at least one of a wellness system 124, a diagnostic system 142, a homing system 152, a content management system 164, a genetics system 170, and/or a third party services system 182. Such external systems are described in more detail below.

Platform 102 may also communicate with one or more external services. In some embodiments, platform 102 may communicate with the one or more external services via APIs 106. External services 122 may include, for example, one or more third party and/or auxiliary systems that integrate and/or communicate with the platform 102 in performing various pet tasks. For example, the external services 122 may include at least one of: a veterinarian, a pet insurance agency, a pet service provider, and the like.

Platform 102 may include database(s) 104 and/or cloud storage 114 that may store information corresponding to one or more pets and/or one or more pet owners. For example, the database(s) 104 and/or cloud storage 114 may store pet profile(s) 118 and/or pet owner profile 120. The database(s)

104 and/or the cloud storage 114 may be located internally or externally to platform 102.

Platform 102 may include a personalized advertising system 108 and/or a payment system 110. The personalized advertising system 108 may create and/or display personalized advertisements to the user. For example, the personalized advertisements may be created based on information contained in pet profile(s) 118 and/or pet owner profile 120. In some embodiments, the personalized advertising system 108 may display the personalized advertisements on a user interface 112 of the platform 102. The payment system 110 may allow the user to create a financial account for a pet and/or perform financial transactions for pet services and/or pet goods (e.g., using pet owner digital wallet 216).

Platform 102 may include a single sign-on 116. The single sign-on 116 may include a unique identifier that may correspond to the pet profile(s) 118 and/or the pet owner profile 120. Each of the pet profile(s) 118 may include information corresponding to a particular pet. The pet owner profile 120 may include information corresponding to a particular pet owner. Additionally, the pet owner profile 120 and/or the pet profile(s) 118 may each have a corresponding avatar and/or virtual presence. The avatar and/or virtual presence may include different attributes that are shared by the pet owner and/or pets. The pet profile(s) 118 and pet owner profile 120 are described in further detail in the description of FIG. 2.

Wellness System

The wellness system 124 may collect, manage, and/or display wellness data of a pet. The wellness system 124 may be an internal component or an external component of platform 102, where the wellness system 124 may communicate with platform 102 via APIs 106.

The wellness system 124 may collect data from one or more smart devices. The wellness system 124 may communicate with the one or more smart devices via one or more APIs. Additionally, in some embodiments, the wellness system may use appware 126 to facilitate the communication and/or the management of the one or more smart devices. For example, appware 126 may communicate with one or more smart devices that may run on an external system. Additionally, for example, appware 126 may run on a user device, where the appware 126 provides a user interface to display the data collected by the one or more smart devices. In some embodiments, appware 126 may manage one or more smart devices. The wellness system 124 may communicate with the one or more smart devices by sending one or more requests to the one or more smart devices. The requests may ask the one or more smart devices to send collected wellness data to the wellness system 124. In some embodiments, the one or more smart devices may automatically send wellness data to the wellness system 124. For example, the one or more smart devices may send the wellness data to the wellness system 124 at regular time intervals (e.g., every 30 seconds, every hour, every day, and the like) and/or whenever new wellness data is collected. In some embodiments, the wellness system 124 may store the wellness data in an internal or external storage. For example, the wellness system 124 may store the wellness data in databases 104 and/or cloud storage 114. Additionally, or alternatively, for example, the wellness system 124 may store the wellness data in the pet profile(s) 118 and/or the pet owner profile 120.

Upon receiving the wellness data from the one or more smart devices, a wellness index scoring system 128 may analyze the wellness data to determine a wellness score. The wellness index scoring system 128 may update the wellness score, where the updating is based on the most recently received wellness data. In some embodiments, the wellness index scoring system 128 may store the wellness score in one or more databases (e.g., database(s) 104) and/or cloud storage (e.g., cloud storage 114). For example, the wellness score may be stored in the pet profile(s) 118 and/or the pet owner profile 120. Additionally, or alternatively, the wellness system 124 may display the wellness score to the user. For example, the wellness system 124 may display the wellness score on a user interface of a user device. This may be accomplished by utilizing the appware 126. Additionally, or alternatively, the wellness system 124 may display the wellness score on one or more of the smart devices.

Example smart devices may include at least one of: a smart collar 130, a smart bed 132, a smart feeder 134, a smart litter box 136, a smart camera 138, and/or the other sensors for collecting a digital image of a pet's life 140.

The smart collar 130 may include a device and/or a sensor that may attach to a pet. For example, the smart collar 130 may attach around the pet's neck The smart collar 130 may detect a pet's activity, location, and eating information, such as physical activity, location, eating habits, drinking habits, and the like. The smart collar 130 may collect the activity, location, and eating information of the pet and send such information to the wellness system 124. In some embodiments, the smart collar 130 may automatically send the activity, location, and eating information to the wellness system 124 after a set period of time. In some embodiments, the smart collar 130 may send the activity, location, and eating information in response to a request from the wellness system 124.

The smart bed 132 may include a device and/or a sensor that may be included in a pet bed. The smart bed 132 may track sleeping information corresponding to the pet. The sleeping information may include the amount of time a pet sleeps in the smart bed 132, how frequently the pet gets up from the smart bed 132, if the pet tosses and turns while sleeping, and the like. The smart bed 132 may send such information to the wellness system 124. In some embodiments, the smart bed 132 may automatically send the sleeping information to the wellness system 124 after a set period of time. In some embodiments, the smart bed 132 may send the sleeping information in response to a request from the wellness system 124.

The smart feeder 134 may include a device and/or a sensor that may be included in a pet food feeder. The smart feeder 134 may track how much food is dispensed for the pet to eat. The smart feeder 134 may send such food dispensing information to the wellness system 124. In some embodiments, the smart feeder 134 may automatically send the food dispensing information to the wellness system 124 after a set period of time. In some embodiments, the smart feeder 134 may send the food dispensing information in response to a request from the wellness system 124.

The smart litter box 136 may include a device and/or a sensor that may be included in a litter box. The smart litter box 136 may track a pet's litter box information. The litter box information may include at least one of: how frequently the pet uses the smart litter box 136, what the pet does in the smart litter box 136, and the like. In some embodiments, the smart litter box 136 may automatically send the litter box information to the wellness system 124. In some embodiments, the smart litter box 136 may automatically send the litter box information to the wellness system 124 after a set period of time. In some embodiments, the smart litter box 136 may send the litter box information in response to a request from the wellness system 124.

The smart camera 138 may include a device and/or a sensor that may be included in a camera. The smart camera 138 may capture behavior information of a pet. The pet's behavior information may include physical activity, eating food from the pet's food dish, eating food from a source different from the pet's food dish, drinking from the pet's drinking dish, drinking from a source different from the pet's drinking dish, and the like. In some embodiments, the smart camera 138 may automatically send the behavior information to the wellness system 124 after a set period of time. In some embodiments, the smart camera 138 may send the behavior information in response to a request from the wellness system 124.

The other sensors for collecting a digital image of a pet's life 140 may include one or more devices and/or one or more sensors that collect data for a digital image of the pet's life. Example collected data may include information regarding the pet's eating behavior, sleeping behavior, drinking behavior, playing behavior, and the like. In some embodiments, the other sensors 140 may automatically send the collected data to the wellness system 124 after a set period of time. In some embodiments, the other sensors 140 may send the collected data in response to a request from the wellness system 124.

Diagnostic System

The diagnostic system 142 may manage a pet's health information and provide personalized diagnostics 144 and/or a personalized wellness plan 146 to the user. The diagnostic system 142 may be an internal component or an external component of platform 102, where the diagnostic system 142 may communicate with platform 102 via APIs 106.

The diagnostic system 142 may manage a pet's heath information (e.g., vaccination records, medical records) by receiving the pet's health information from one or more external services 150 (e.g., veterinarians, clinics, pet hospital, and the like). The diagnostic system 142 may store the pet's health information in the pet profile(s) 118. In an embodiment, the diagnostic system 142 may communicate the pet's health information using APIs 106.

The diagnostic system may create personalized diagnostics 144 and/or a personalized wellness plan 146 based on the pet's health information. The personalized diagnostics 144 may include one or more diagnoses (e.g., ear infection, eye infection, and the like) of medical conditions for the pet. The personalized diagnostics 144 may be based on diagnoses made by the external services 150. In some embodiments, the personalized diagnostics 144 may be based on diagnoses made by one or more machine learning models. The personalized wellness plan 146 may include one or more recommendations regarding eating events, exercise events, health checks and wellness visits, and the like, which may be based on the pet's heath information. The personalized wellness plan 146 may be based on recommendations made by the external services 150. The personalized wellness plan 146 may be based on information included in the pet profile(s) 118. In some embodiments, the personalized wellness plan may be based on one or more recommendations made by one or more machine learning models.

The health portal 148 may provide access to one or more parties who wish to retrieve the personalized diagnostics 144, personalized wellness plan 146, and/or the pet's health information from the pet profile(s) 118. The health portal 148 may be internal or external to the diagnostic system 142. Additionally, the health portal 148 may include a user interface. For example, a groomer may access the health portal 148 to retrieve the pet's vaccination records from diagnostic system 142.

The diagnostic system 142 may communicate with external services 150, such as veterinarians, clinics, pet hospital, and the like. For example, an external service 150 (e.g., veterinarian) may send updated vaccine or medical records to the diagnostic system 142, where the diagnostic system 142 may then store such updated vaccine or medical records in the pet profile(s) 118. Additionally, for example, the diagnostic system may update the personalized diagnostics 144 and/or the personalized wellness plan 146 based on the updated vaccine or medical records.

In some embodiments, the diagnostic system 142 may include information to authenticate the pet. For example, social media websites frequently require that a user is authenticated in order to label the user as "verified" (e.g., a blue checkmark). The diagnostic system 142 may contain information corresponding to a physical examination of the pet. Such information may include authentication information of the pet. For example, the authentication information may include a confirmation of the pet's breed, gender, image, etc. Such authentication information may be used by a social media website to authenticate the pet as a "verified" user.

Homing System

The homing system 152 may match a future pet owner with a pet and provide additional support for the future pet owner. The homing system 152 may be an internal component or an external component of platform 102, where the homing system 152 may communicate with platform 102 via APIs 106.

The homing system 152 may match a future pet owner with a particular pet using a personalized matching module 154 and/or a search engine 156. The personalized matching module 154 may use user information (e.g., user location, user age, and the like) from the future pet owner (e.g., from the pet owner profile 120) to automatically search for one or more pets that are best suited for the future pet owner. In some embodiments, the personalized matching module 154 may use one or more machine learning models to determine the best pet matches for the future pet owner. The search engine 156 may allow the future pet owner to search for one or more pets. The search engine 156 may include different search filters (e.g., filtering by breed, age, size, weight, and the like), which may allow the user to filter the results of the one or more pets.

Both the personalized matching module 154 and/or the search engine 156 may retrieve results from the external services 162. The external services 162 may include one or more of: a pet adoption agency, a shelter, a pet breeder, and the like. When the personalized matching module 154 and/or the search engine 156 is performing a search for one or more pets, the personalized matching module 154 and/or the search engine 156 may send one or more requests to the external services 162 for available pets that fit one or more parameters contained in the one or more requests. Upon receiving the one or more requests, the external services 162 may search one or more databases for one or more matching pets. The external services 162 may send a response to the personalized matching module 154 and/or the search engine 156. The response may include the one or more matching pets. Alternatively, for example, if no matching pets were found, the response may include an indicator that no matching pets were found. In some embodiments, the homing system 152 may store the one or more matching pets in a database, such as an internal database or an external database (e.g., database 104).

The homing system 152 may display the one or more matching pets to the future pet owner, along with an option for the future pet owner to adopt and/or purchase the one or more matching pets. The homing system 152 may also facilitate the adoption and/or purchase of the one or more matching pets. In some embodiments, the homing system 152 may communicate with the external services 162 to facilitate the adoption and/or purchase of the one or more matching pets.

Once the future pet owner purchases and/or adopts the pet, the homing system 152 may store and/or manage the pet's adoption/registration record 160. In some embodiments, the homing system 152 may receive all (or part of) the pet's adoption/registration record 160 from the external services. In some embodiments, the homing system 152 may store the pet's adoption/registration record 160 in the pet profile(s) 118. Additionally, or alternatively, the homing system 152 may store the pet's adoption/registration record in the pet owner profile 120. In some embodiments, the homing system 152 may store the pet's adoption/registration record 160 in an internal or external database.

The homing system 152 may provide additional support for the future pet owner by providing personalized recommendations 158 to the pet owner. The personalized recommendations 158 may be based characteristics of the pet that the future pet owner purchased and/or adopted. Example personalized recommendations 158 may include a recommended pet food, a recommended pet provider, recommended pet supplies, and the like. In some embodiments, the personalized recommendations 158 may be based on communications with one or more of the external services. For example, the homing system 152 may communicate with the content management system 164 to receive personalized content 168, and then make personalized recommendations 158 based on the personalized content 168.

Content Management System

The content management system 164 may provide personalized content 168 to a user. The content management system 164 may be an internal component or an external component of platform 102, where the content management system 164 may communicate with platform 102 via APIs 106.

The content management system 164 may retrieve personalized content 168 and display such personalized content 168 to the user. The personalized content 168 may include at least one of: an article, a blog post, an online forum, an advertisement, and the like. The personalized content 168 may also include recommendations that are specific towards the pet and/or user. The recommendations may include food recommendations, activity recommendations, product recommendations, resource recommendations (e.g., books, articles, and the like), third party services recommendations (e.g., groomer, trainer, boarding), and the like. The personalized content 168 may be personalized based on pet profile(s) 118 and/or pet owner profile 120. The content management system 164 may display the personalized content 168 via a user interface of a user device. In some embodiments, the content management system 164 may retrieve the personalized content 168 from the external services 166. The external services 166 may include an electronic magazine, one or more databases, one or more social media posts, and the like. In some embodiments, the content management system 164 may retrieve the personalized content 168 from other sources, such as database(s) 104, cloud storage 114, and personalized advertising system 108. In some embodiments, the content management system 164 may create personalized content 168 based on communications with the other external systems (e.g., wellness system 124, diagnostic system 142, homing system 152, genetics system 170, third party services system 182, etc.). For example, the content management system 164 may receive the personalized wellness plan 146 from diagnostic system 142. The personalized content 168 may then be based on (or include) information from the personalized wellness plan 146.

Genetics System

The genetics system 170 may analyze and/or monitor a pet's genetic data. The genetics system 170 may be an internal component or an external component of platform 102, where the genetics system 170 may communicate with platform 102 via APIs 106.

The genetics system 170 may include genetic data analysis 172, genetic data monitoring 174, and/or personalized recommendations 176. Additionally, the genetic data analysis 172 and/or the genetic data monitoring 174 may communicate with external services 180 to assist with the analysis and/or the monitoring of the genetic data. The external services may include a laboratory, a clinic, a veterinarian, and the like.

The genetic data analysis 172 may receive genetic data belonging to a pet. In some embodiments, the genetic data analysis 172 may receive the genetic data from a genetic data retrieval system 178. The genetic data retrieval system 178 may retrieve and store genetic data belonging to one or more pets. Additionally, the genetic data analysis may receive genetic data from the genetic data retrieval system 178, where the received genetic data is used in the analysis of the genetic data belonging to the pet. The genetic data analysis 172 may analyze the genetic data to determine abnormalities, potential genetic traits, familial relationships, and the like. In some embodiments, the genetic data analysis 172 may communicate with external services 180 to assist with the analysis of the genetic data. For example, the genetic data analysis 172 may send genetic data information to a laboratory for the laboratory to perform the analysis of the genetic data.

The genetic data monitoring 174 may monitor the genetic data belonging to a pet to determine any changes in the genetic data. For example the genetic data monitoring 174 may receive new genetic data and compare the new genetic data to previously stored genetic data. The comparing may lead the genetic data monitoring 174 to determine that there is an abnormality or an improvement in the genetic data. In some embodiments, the genetic data monitoring 174 may communicate with the external services 180, in order for the external services 180 to analyze the genetic data and determine if there are any changes.

The genetics system 170 may provide personalized recommendations 176 to the user. For example, the genetics system 170 may provide personalized recommendations 176 to the user via a user interface of a user device. In some embodiments, the personalized recommendations may be based on the genetic data analysis 172 and/or the genetic data monitoring 174. The personalized recommendations 176 may include a pet food recommendation, an exercise recommendation, a pet item recommendation, health checks or wellness visits, and the like. In some embodiments, the personalized recommendations 176 may be based on communications with one or more of the external services. For example, the genetics system 170 may communicate with the diagnostic system 142. The genetics system 170 may send a request to the diagnostic system 142 for a personalized wellness plan 146. The request may include, for example, the genetic data analysis 172 and/or the genetic data monitoring 174. The diagnostic system 142 may communicate a personalized wellness plan 146 to the genetics system 170, where the personalized wellness plan 146 may be based on the genetic data analysis 172 and/or the genetic data monitoring 174. The genetics system 170 may make personalized recommendations 176 to the user based on the personalized wellness plan 146.

In some embodiments, the genetics system 170 may include information to authenticate the pet. For example, social media websites frequently require that a user is authenticated in order to label the user as "verified" (e.g., a blue checkmark). The genetics system 170 may contain information corresponding to a physical examination of the pet. Such information may include authentication information of the pet. For example, the authentication information may include a confirmation of the pet's breed, gender, image, etc. Such authentication information may be used by a social media website to authenticate the pet as a "verified" user.

Third Party Services System

The third party services system 182 may allow a user to search for and reserve different external services 190, such as groomers, trainers, veterinarians, holistic care (e.g., nutritionist, naturopathic), and the like. The third party services system 182 may be an internal component or an external component of platform 102, where the third party services system 182 may communicate with platform 102 via APIs 106.

The third party services system 182 may include a search engine 184, a booking engine 186, and/or a management component 188.

The search engine 184 may allow the user, such as a pet owner, to search for external services 190 to reserve for the user's pet. The search engine 184 may include filtering functionality to facilitate a fine-tuned search. The filtering functionality may include universal filtering and/or service specific filtering. For example, the universal filtering may include filtering the external services 190 by location, price range, and/or ratings. Additionally, for example, the service specific filtering may include filtering the external services 190 by breed specialty, health issues, and/or behavioral needs.

The booking engine 186 may allow the user to reserve the external services 190. For example, after using the search engine 184 to search for external services 190, the user may use the booking engine 186 to reserve a particular service of the external services 190. The booking engine 186 may present open dates and time slots, which may correspond to the selected external service 190. The user may then user the booking engine 186 to select a date and/or time from the displayed open dates and time slots. Upon the finalization of the booking, the user may receive an instant confirmation of the booking, such as via text or email. The user may also have the ability to instantly pay for the booked service. Alternatively, the user may be able to pay upon the finalization of the service. The user may be able to upload photos and include notes to the external service 190. For example, the user may upload dog photos to a groomer, or make a note that the user's dog has a limp.

The management component 188 may provide functionality to manage different external services 190. For example, the management component 188 may provide the functionality for external services 190 to register and/or be removed from the third party services system 182. The management component 188 may communicate with one or more databases (e.g., database(s) 104) and/or cloud storage (e.g., cloud storage 114) to store information (e.g., a name, a business identifier, a specialty, and the like) corresponding to the external services 190.

Exemplary Pet Owner Profile and Pet Profile(s)

Figure 2:
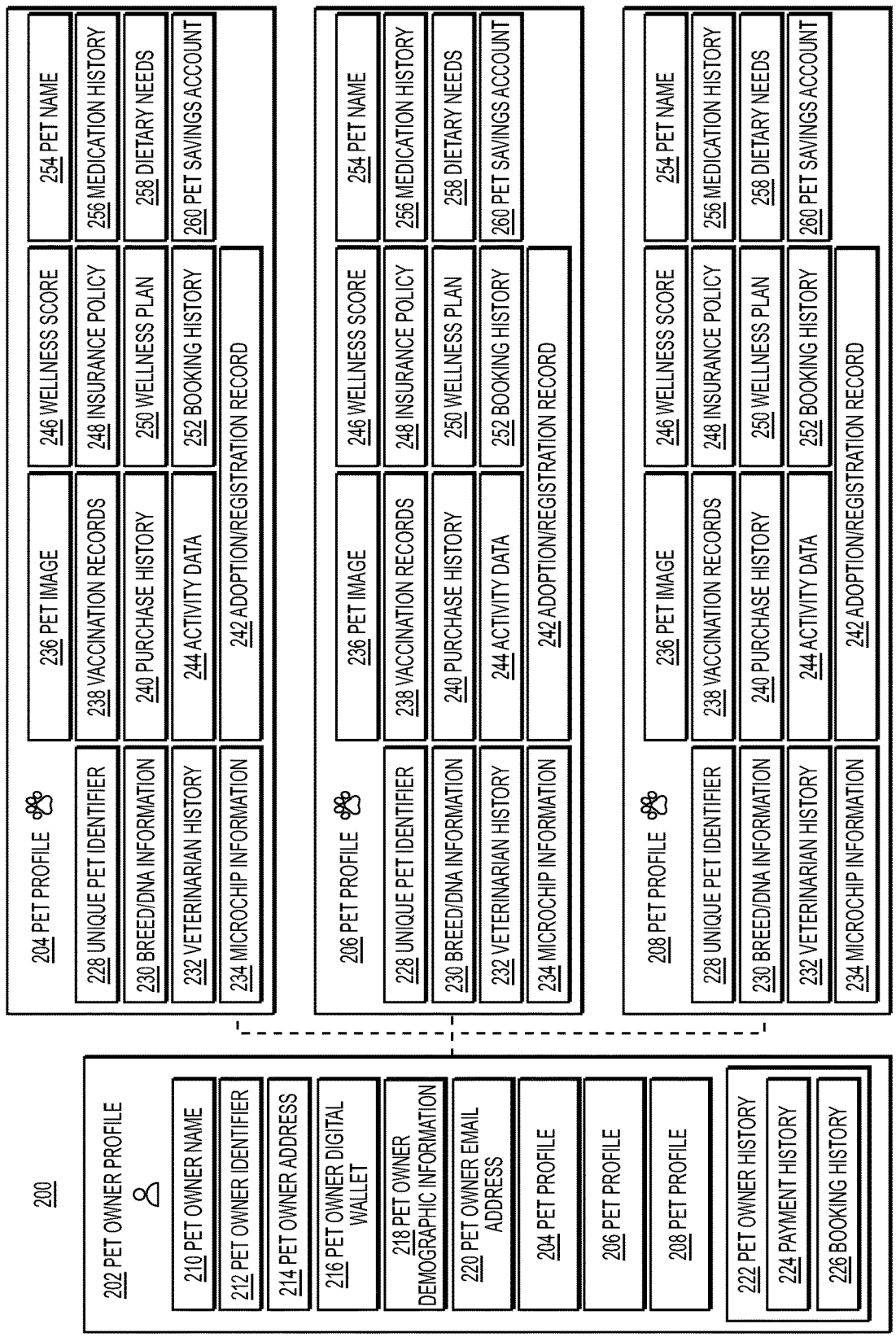
FIG. 2 depicts an exemplary environment of a pet owner profile and corresponding pet profiles, according to one or more embodiments.

FIG. 2 depicts an exemplary environment 200 of a pet owner profile 202 and corresponding pet profiles that may be utilized with the techniques presented herein. Notably, exemplary platform environment 200 may complement exemplary platform environment 100, with pet owner profile 202 corresponding to pet owner profile 120 of FIG. 1. Additionally, pet profile 204, pet profile 206, and/or pet profile 208 may correspond to pet profiles(s) 118 of FIG. 1.

Pet owner profile 202 may include at least one of: a pet owner name 210, a pet owner identifier 212, a pet owner address 214, a pet owner digital wallet 216, pet owner demographic information 218, a pet owner email address 220, at least one pet profile (e.g., pet profile 204, pet profile 206, pet profile 208) and/or at least one identifier associated with the at least one pet profile, and/or a pet owner history 222. The pet owner name 210 may include a name of the pet owner. The pet owner identifier 212 may include a unique identifier that may be used to locate the pet owner profile 202. In some embodiments, the pet owner identifier 212 may allow for tracking of some or all of the user's activities. The pet owner address 214 may include a physical address of the pet owner. The pet owner digital wallet 216 may include payment information, such as credit card information, cryptocurrency information, and the like. The pet owner demographic information 218 may include a particular demographic of the pet owner. The pet owner email address 220 may include an email address of the pet owner. The pet owner profile may include at least one pet profile (e.g., pet profile 204, pet profile 206, pet profile 208). In some embodiments, in lieu of including an entirety of the at least one pet profile, the pet owner profile 202 may include at least one identifier associated with the at least one pet profile (e.g., unique pet identifier 228). Each of the pet profiles may correspond to a pet that belongs to the pet owner. The number of pet profiles may be dynamic, where the pet profiles may adjust according to the number of pets that belong to the user.

The pet owner history 222 may include a payment history 224 and/or a booking history 226. The payment history 224 may include financial transactions of the pet owner. In some embodiments, the payment history 224 may correspond to activity of the pet owner digital wallet 216. In some embodiments, the payment history 224 may be tracked and analyzed to provide for targeted advertising (e.g., of personalized advertising system 108) and/or recommendations to the pet owner. The booking history 226 may include previous bookings of third party services that were made by the user. In some embodiments, the booking history 226 may be tracked and analyzed to provide for targeted advertising (e.g., of personalized advertising system 108) and/or recommendations to the pet owner.

Pet profile 204, pet profile 206, and/or pet profile 208 may each correspond to a different pet that belongs to the pet owner of the pet owner profile 202. The pet owner may have more or less than three pets. The number of pet profiles may be dynamic, where the number of pet profiles corresponds to the number of pets that belong to the pet owner. In some embodiments, the pet owner may want only a subset of the pet owner's pets to have pet profiles.

Pet profiles 204, 206, and/or 208 may each include at least one of: a unique pet identifier 228, breed/DNA information 230, veterinarian history 232, microchip information 234, a pet image 236, vaccination records 238, a purchase history 240, an adoption/registration record 242, activity data 244, a wellness score 246, an insurance policy 248, a wellness plan 250, a booking history 252, a pet name 254, medication history 256, dietary needs 258, and/or a pet savings account 260.

The unique pet identifier 228 may include a unique identifier that may be used to locate the corresponding pet profile (e.g., pet profiles 204, 206, and/or 208). In some embodiments, the unique pet identifier 228 may allow for tracking of some or all of activities corresponding to the pet.

The pet image 236 may include to a photograph, drawing, virtual presence, and/or avatar of the pet. The pet name 254 may include the name of the pet and/or any nicknames. The insurance policy 248 may include a pet insurance policy for the pet. The purchase history 240 may include purchases made for the pet. The pet savings account 260 may include a financial savings account for the pet. In some embodiments, the pet image 236, the pet name 254, the purchase history 240, pet savings account 260, and/or the insurance policy 248 may have been received from one or more of the external systems.

The breed/DNA information 230 may correspond to the breed and/or DNA information of the pet. In some embodiments, the breed/DNA information 230 may have been received from one or more of the external systems. For example, the breed/DNA information 230 may have been received from genetics system 170.

The veterinarian history 232 may include the details of the pet's visit(s) to a veterinarian. The veterinarian history 232 may also include notes from the vet and/or possible diagnoses and treatments. The vaccination records 238 may include one or more vaccination records of vaccinations administered to the pet. The medication history 256 may include details of the medications that the pet currently takes and/or has taken in the past. The dietary needs 258 may include information regarding food that the pet should eat and/or food that the pet should avoid. The wellness plan 250 may correspond to a wellness plan for the pet. In some embodiments, the wellness plan 250 may have been determined based on personalized wellness plan 146. In some embodiments, the veterinarian history 232, vaccination records 238, dietary needs 258, wellness plan 250, and/or the medication history 256 may have been received from one or more of the external systems. For example, the veterinarian history 232, vaccination records 238, dietary needs 258, wellness plan 250, and/or the medication history 256 may have been received from diagnostic system 142.

The microchip information 234 may include a microchip number of the pet. For example, the microchip may have been inserted into the pet to track the pet. The adoption/registration record 242 may include documentation of the adoption or purchase of the pet. In some embodiments, the microchip information 234 and/or adoption/registration record 242 may have been received from one or more of the external systems. For example, the microchip information 234 and/or adoption/registration record 242 may have been received from homing system 152.

The activity data 244 may include data corresponding to physical activities, sleep activities, and/or food activities of the pet. For example, the activity data may be collected by a smart collar 130, a smart bed 132, a smart feeder 134, a smart litter box 136, a smart camera 138, and/or the other sensors for collecting a digital image of a pet's life 140. The wellness score 246 may include data corresponding to a wellness score produced by wellness index scoring system 128. In some embodiments, the activity data 244 and/or the wellness score 246 may have been received from one or more of the external systems. For example, the activity data 244 and/or the wellness score 246 may have been received from wellness system 124.

The booking history 252 may include data corresponding to one or more bookings of a third party service (e.g., groomer, trainer, and the like). In some embodiments, the booking history 252 may have been received from one or more of the external systems. For example, the booking history 252 may have been received from the third party services system 182.

Exemplary Method for Dynamically Managing Petcare Data

Figure 3:
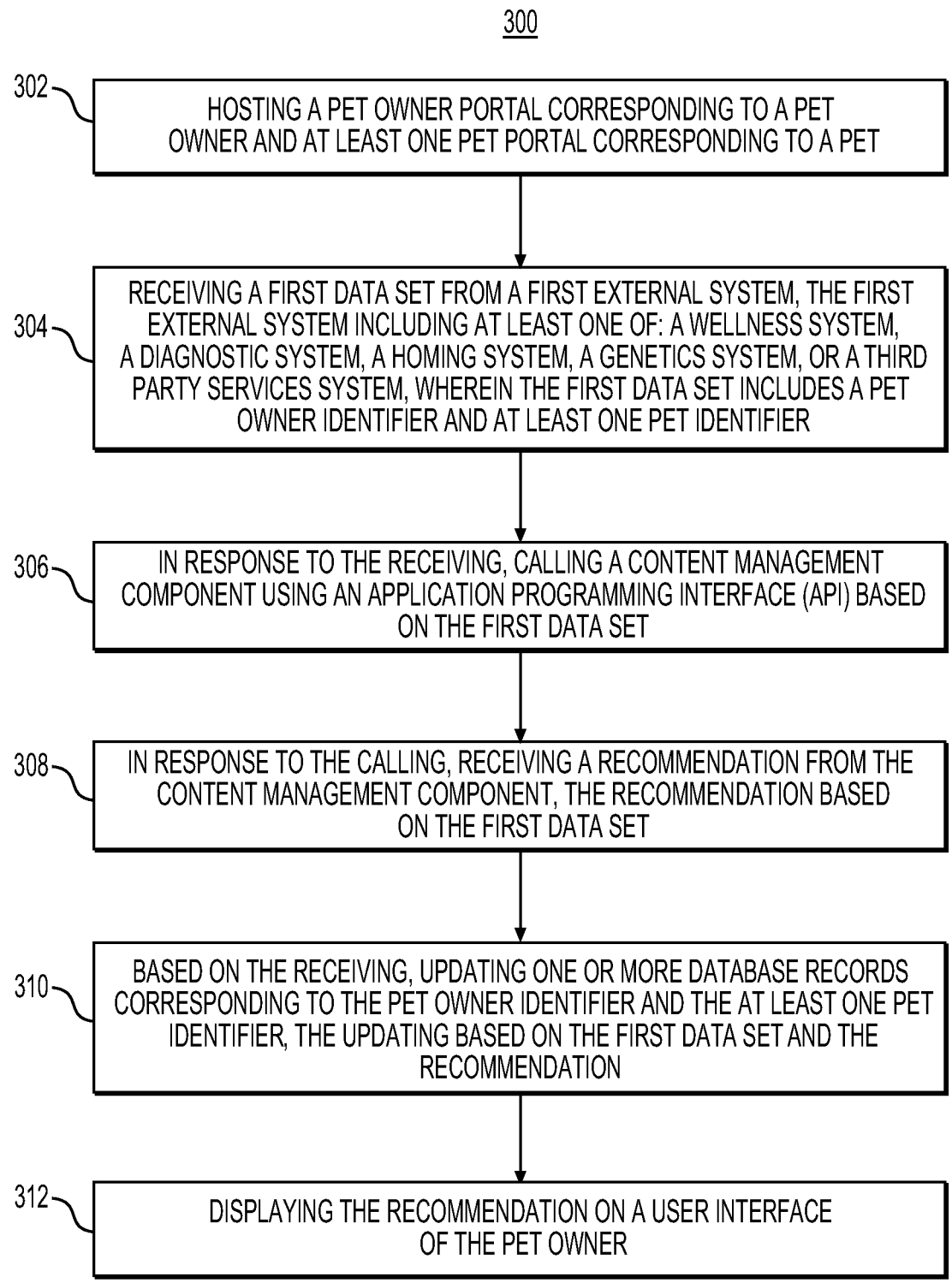
FIG. 3 depicts a flowchart of an exemplary embodiment for dynamically managing electronic transactions of petcare data, according to one or more embodiments.

FIG. 3 illustrates an exemplary method 300 of an exemplary embodiment for dynamically managing electronic transactions of petcare data, according to one or more embodiments. Notably, method 300 may be performed by one or more processors of a server that is in communication with one or more user devices and other external system(s) via a network. However, it should be noted that method 300 may be performed by any one or more of the server, one or more user devices, or other external systems.

The method may include hosting, by one or more processors, a user portal corresponding to at least one user and at least one pet, the user portal including at least one user profile (e.g., pet owner profile 120) and at least one pet profile (e.g., pet profile(s) 118) (Step 302). The user portal may be accessible by a single sign-on identifier (e.g., single sign-on 116). In some embodiments, the user portal may include a user interface for interacting with one or more users. The at least one user profile may correspond to a pet owner. The at least one user profile may include at least one of: a name, an address, a digital wallet, demographic data, an email address, payment history data, booking history data, or the at least one pet identifier. The at least one pet profile may correspond to at least one pet that belongs to the pet owner. The at least one pet profile may include at least one of: a name, an image, a wellness score, at least one vaccination record, insurance policy data, medication history data, breed data, DNA data, wellness plan data, veterinarian history data, an adoption record, a registration record, booking history data, microchip data, activity data, insurance information data, or pet savings account data.

The method may include receiving, by the one or more processors, a first data set from a first external system, the first external system including at least one of: a wellness system (e.g., wellness system 124), a diagnostic system (e.g., diagnostic system 142), a homing system (e.g., homing system 152), a genetics system (e.g., genetics system 170), or a third party services system (e.g., third party services system 182), wherein the first data set includes at least one user identifier (e.g., pet owner identifier 212) and/or at least one pet identifier (e.g., unique pet identifier 228) (Step 304). The first data set may include data that the first external system received from an external service, data that the first external system created, data that the first external system managed, and the like. The first data set may include the at least one user identifier that may be a unique identifier that identifies the pet owner (e.g., pet owner identifier 212). Additionally, for example, the at least one user identifier may identify the at least one user profile (e.g., pet owner profile 120). The first data set may also include the at least one pet identifier that may be a unique identifier (e.g., unique pet identifier 228) that identifies at least one pet belonging to the pet owner. Additionally, for example, the at least one pet identifier may identify the pet profile(s) (e.g., pet profile(s) 118). For example, the data set may be received from the wellness system 124, where the data set includes a wellness score, a pet owner identifier 212, and a unique pet identifier 228.

In response to the receiving, the method may also include calling, by the one or more processors, a content management component (e.g., content management system 164) using an application programming interface (API) based on the first data set (Step 306). For example, calling the content management component may include sending a request to the content management component, where the request may include the at least one user identifier and/or the at least one pet identifier. The request may also include other pet or user-related data included in the first data set. In some embodiments, the method may include using the at least one user identifier and/or the at least one pet identifier to access the pet owner profile (e.g., pet owner profile 120) and/or the pet profile (e.g., pet profile(s) 118) to gather additional information, where the additional information may be used when calling the content management component.

In response to the calling, the method may also include receiving, by the one or more processors, a recommendation from the content management component, the recommendation based on the first data set (Step 308). For example, upon receiving the call, the content management component may utilize information received in the call, such as some or all of the data in the first data set, to determine a recommendation (e.g., by using personalized content 168). The recommendation may include at least one food recommendation, activity recommendation, product recommendation, resource recommendation (e.g., books, articles, and the like), and/or third party service recommendation.

The method may also include, based on the receiving, updating, by the one or more processors, one or more database records corresponding to the at least one user identifier and/or the at least one pet identifier, where the updating may be based on the first data set and/or the recommendation (Step 310). In some embodiments, one or more databases (e.g., database(s) 104) may store the one or more database records. Additionally, the one or more database records may store some or all of the at least one user profile and/or the at least one pet profile. For example, the one or more database records may be identified based on whether the one or more database records correspond to the at least one user identifier and/or the at least one pet identifier. The one or more database records may be updated to include some or all of the first data set, as well as include the recommendation. In some embodiments, if no database records corresponding to the at least one user identifier and the at least one pet identifier exist, the method may include creating one or more database records.

The method may also include displaying, by the one or more processors, the recommendation on a user interface (e.g., user interface 112) of the user portal (Step 312). For example, the user interface may display the recommendation and a corresponding link. The link may allow the user to further engage with the recommendation (e.g., purchase a product, reserve services, and the like). In some embodiments, the method may include tracking and/or analyzing whether the user engages with the recommendation. The method may further include tailoring future recommendations based on whether the user engages with the recommendation. For example, the content management component (e.g., content management system 164) may receive feedback indicating whether the user engages with the recommendation, where the content management component may tailor future recommendations based on such feedback.

The method may further include receiving, by the one or more processors, a second data set from a second external system, the second external system including at least one of: the wellness system (e.g., wellness system 124), the diagnostic system (e.g., diagnostic system 142), the homing system (e.g., homing system 152), the genetics system (e.g., genetics system 170), or the third party services system (e.g., third party services system 182), wherein the second data set includes the at least one user identifier and the at least one pet identifier. The second data set may include data that the second external system received from an external service, data that the second external system created, data that the second external system managed, and the like. In some embodiments, the at least one user identifier (e.g., pet owner identifier 212) and/or the at least one pet identifier (e.g., unique pet identifier 228) in the second data set may be similar to the at least one user identifier and/or the at least one pet identifier in the second data set.

In response to the receiving, the method may also include calling, by the one or more processors, the content management component (e.g., content management system 164) using the API based on the second data set. For example, calling the content management component may include sending a request to the content management component, where the request may include the at least one user identifier and/or the at least one pet identifier. The request may also include other pet or user-related data included in the second data set. In some embodiments, the method may include using the at least one user identifier and/or the at least one pet identifier to access the pet owner profile (e.g., pet owner profile 120) and/or the pet profile (e.g., pet profile(s) 118) to gather additional information, where the additional information may be used when calling the content management component.

In response to the calling, the method may also include receiving, by the one or more processors, a second recommendation from the content management component, the second recommendation based on the second data set. For example, upon receiving the call, the content management component may utilize information received in the call, such as some or all of the data in the second data set, to determine a recommendation (e.g., by using personalized content 168). The recommendation may include at least one food recommendation, activity recommendation, product recommendation, resource recommendation (e.g., books, articles, and the like), and/or third party service recommendation.

Based on the receiving, the method may also include updating, by the one or more processors, the one or more database records corresponding to the at least one user identifier and/or the at least one pet identifier, the updating based on the second data set and the second recommendation. In some embodiments, one or more databases (e.g., database(s) 104) may store the one or more database records. Additionally, the one or more database records may store some or all of the at least one user profile and/or the at least one pet profile. For example, the one or more database records may be identified based on whether the one or more database records correspond to the at least one user identifier and/or the at least one pet identifier. The one or more database records may be updated to include some or all of the second data set, as well as include the recommendation. In some embodiments, if no database records corresponding to the at least one user identifier and the at least one pet identifier exist, the method may include creating one or more database records.

The method may also include displaying, by the one or more processors, at least one personalized advertisement on the user interface, where the at least one personalized advertisement may be based on the first data set and/or the second data set. In some embodiments, the at least one personalized advertisement may be received from a personalized advertising system (e.g., personalized advertising system 108). The at least one personalized advertisement may include content that is based on the first data set or the second data set. The at least one personalized advertisement may include an advertised product and/or service. In some embodiments, the at least one personalized advertisement may also include a link to the advertised product and/or service, where the link may allow a user to gain more information and/or purchase the advertised product and/or a service. In some embodiments, the method may include tracking and/or analyzing whether the user engages with the advertisement.

In some embodiments, the first external system and/or the second external system may be the wellness system (e.g., wellness system 124). Additionally, the first data set and/or the second data set may include activity data captured by a sensor worn by the at least one pet (e.g., smart collar 130, other sensors 140). In some embodiments, the first data set and/or the second data set may include activity data captured by a sensor (e.g., smart collar 130, smart bed 132, smart feeder 134, smart litter box 136, smart camera 138, and/or the other sensors for collecting a digital image of a pet's life 140).

In some embodiments, the first external system and/or the second external system may be the diagnostic system (e.g., diagnostic system 142). Additionally, the first data set and/or the second data set may include wellness plan data (e.g., personalized wellness plan 146) and/or diagnostic data (e.g., personalized diagnostics 144) corresponding to the at least one pet. The wellness plan data and/or the diagnostic data may be based on the at least one pet profile (e.g., pet profile(s) 118).

In some embodiments, the first external system and/or the second external system may be the homing system (e.g., homing system 152). Additionally, the first data set and/or the second data set may include an adoption record (e.g., adoption/registration record 160), a registration record (e.g., adoption/registration record 160), and/or a personalized match (e.g., personalized matching module 154) based on the at least one user profile and/or the at least one pet profile.

In some embodiments, the first external system and/or the second external system may be the genetics system (e.g., genetics system 170). Additionally, the first data set and/or the second data set may include a genetic data analysis (e.g., genetic data analysis 172). In some embodiments, the first data set and/or the second data set may include genetic data monitoring (e.g., genetic data monitoring 174) and/or personalized recommendations (e.g., personalized recommendations 176).

In some embodiments, the first external system and/or the second external system may be the third party services system (e.g., third party services system 182). Additionally, the first data set and/or the second data set may include booking data (e.g., from booking engine 186) and/or a communication from an external service (e.g., external services 190).

Although FIG. 3 shows example blocks of exemplary method 300, in some implementations, the exemplary method 300 may include additional blocks, fewer blocks, different blocks, or differently arranged blocks than those depicted in FIG. 3. Additionally, or alternatively, two or more of the blocks of the exemplary method 300 may be performed in parallel.

Additional Exemplary Method for Dynamically Managing Petcare Data

Figure 4:
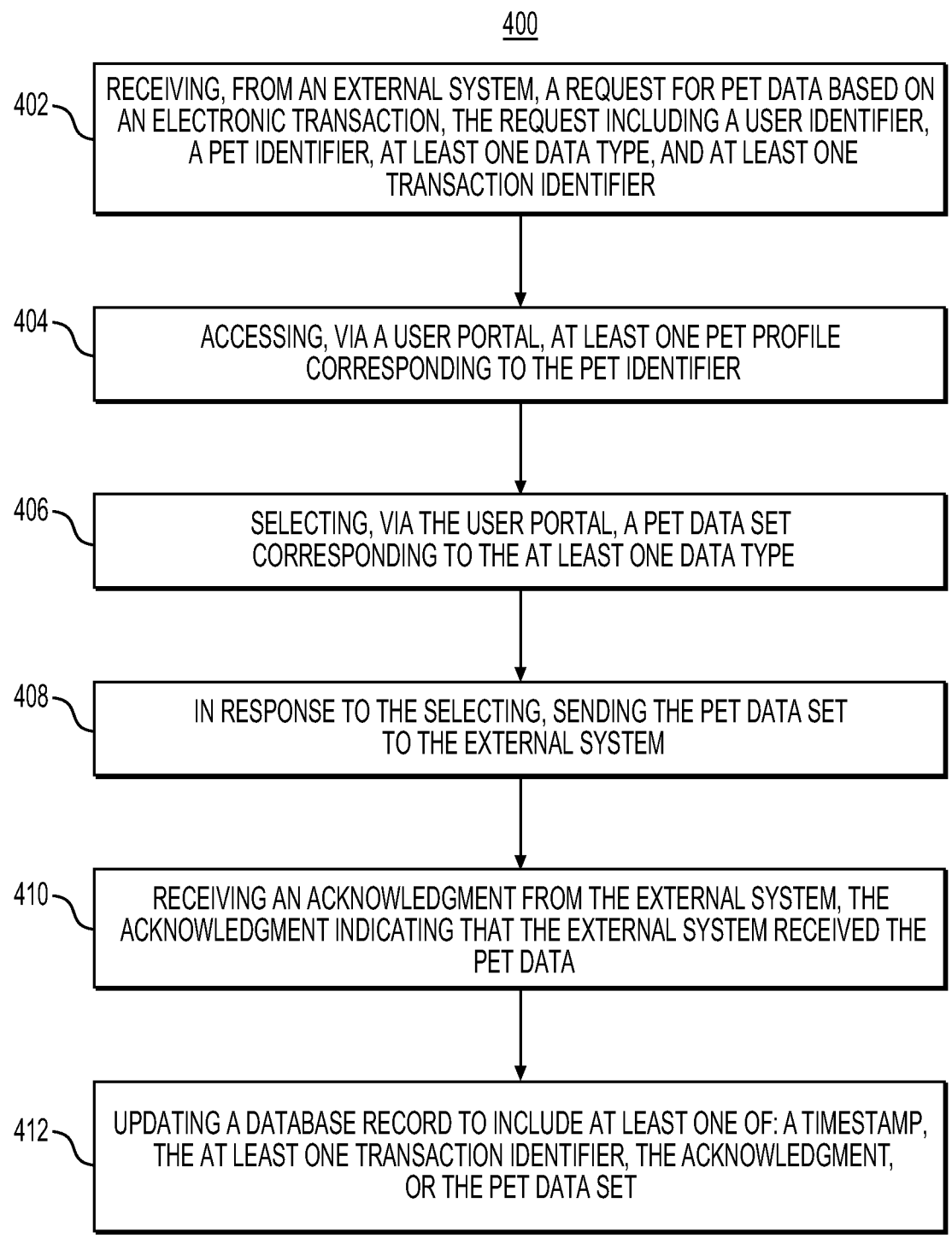
FIG. 4 depicts a flowchart of an exemplary embodiment for dynamically managing electronic transactions of petcare data, according to one or more embodiments.

FIG. 4 illustrates an exemplary method 400 of an exemplary embodiment for dynamically managing electronic transactions of petcare data, according to one or more embodiments. Notably, method 400 may be performed by one or more processors of a server that is in communication with one or more user devices and other external system(s) via a network. However, it should be noted that method 400 may be performed by any one or more of the server, one or more user devices, or other external systems.

The method may include receiving, from an external system, a request for pet data based on an electronic transaction, the request including a user identifier, a pet identifier, at least one data type, and at least one transaction identifier (Step 402). In some embodiments, the request may include just one of a user identifier or a pet identifier. The user identifier may include a pet owner identifier (e.g., pet owner identifier 212) that may correspond to a pet owner profile (e.g., pet owner profile 202). The pet identifier may correspond to a unique pet identifier (e.g., unique pet identifier 228) of a pet belonging to the pet owner. The at least one data type may include at least one of: a name, an image, a wellness score, at least one vaccination record, insurance policy data, medication history data, breed data, DNA data, wellness plan data, veterinarian history data, an adoption record, a registration record, booking history data, microchip data, activity data, insurance information data, and/or pet savings account data. The at least one transaction identifier may include a unique identifier that corresponds to the electronic transaction. The electronic transaction may correspond to an event where pet data is received, created, updated, and the like. Additionally, the external system may include at least one of: a wellness system (e.g., wellness system 124), a diagnostic system (e.g., diagnostic system 142), a homing system (e.g., homing system 152), a genetics system (e.g., genetics system 170), or a third party services system (e.g., third party services system 182).

The method may also include accessing, via a user portal, at least one pet profile corresponding to the pet identifier (Step 404). The user portal may be accessible by a single sign-on identifier (e.g., single sign-on 116). In some embodiments, the user portal may include a user interface for interacting with one or more users. The method may include searching for at least one pet profile (e.g., pet profile(s) 118) corresponding to the unique pet identifier (e.g., unique pet identifier 228).

The method may also include selecting, via the user portal, a pet data set corresponding to the at least one data type (Step 406). The pet data set may include all or some of the values corresponding to the at least one data type. In some embodiments, the selecting may be performed by a user. For example, the user may select the at least one data type via the user portal. In some embodiments, the selecting may be automatically performed.

The method may also include in response to the selecting, sending the pet data set to the external system (Step 408). For example, the selected pet data set may be sent via API access. The method may also include receiving an acknowledgment from the external system, the acknowledgment indicating that the external system received the pet data set (Step 410). In some embodiments, the acknowledgement may include a unique confirmation identifier.

The method may also include updating a database record to include at least one of: a timestamp, the at least one transaction identifier, the acknowledgment, or the pet data set (Step 412). In some embodiments, one or more databases (e.g., database(s) 104) may store the database record. The database record may record the transaction of sending the pet data set to the external system. The timestamp may include the date and/or time that the transaction occurred. The transaction identifier may identify the request from the external system. The acknowledgment may include the unique confirmation identifier. The pet data set may include some or all of the values that were sent to the external system.

The method may also include, in response to receiving the request for the pet data, sending a request to a second external system for the pet data. The method may also include receiving the pet data from the second external system. Additionally, the second external system may include at least one of: a wellness system (e.g., wellness system 124), a diagnostic system (e.g., diagnostic system 142), a homing system (e.g., homing system 152), a genetics system (e.g., genetics system 170), or a third party services system (e.g., third party services system 182).

Although FIG. 4 shows example blocks of exemplary method 400, in some implementations, the exemplary method 400 may include additional blocks, fewer blocks, different blocks, or differently arranged blocks than those depicted in FIG. 4. Additionally, or alternatively, two or more of the blocks of the exemplary method 400 may be performed in parallel.

Exemplary Platform Flow

Figure 5:
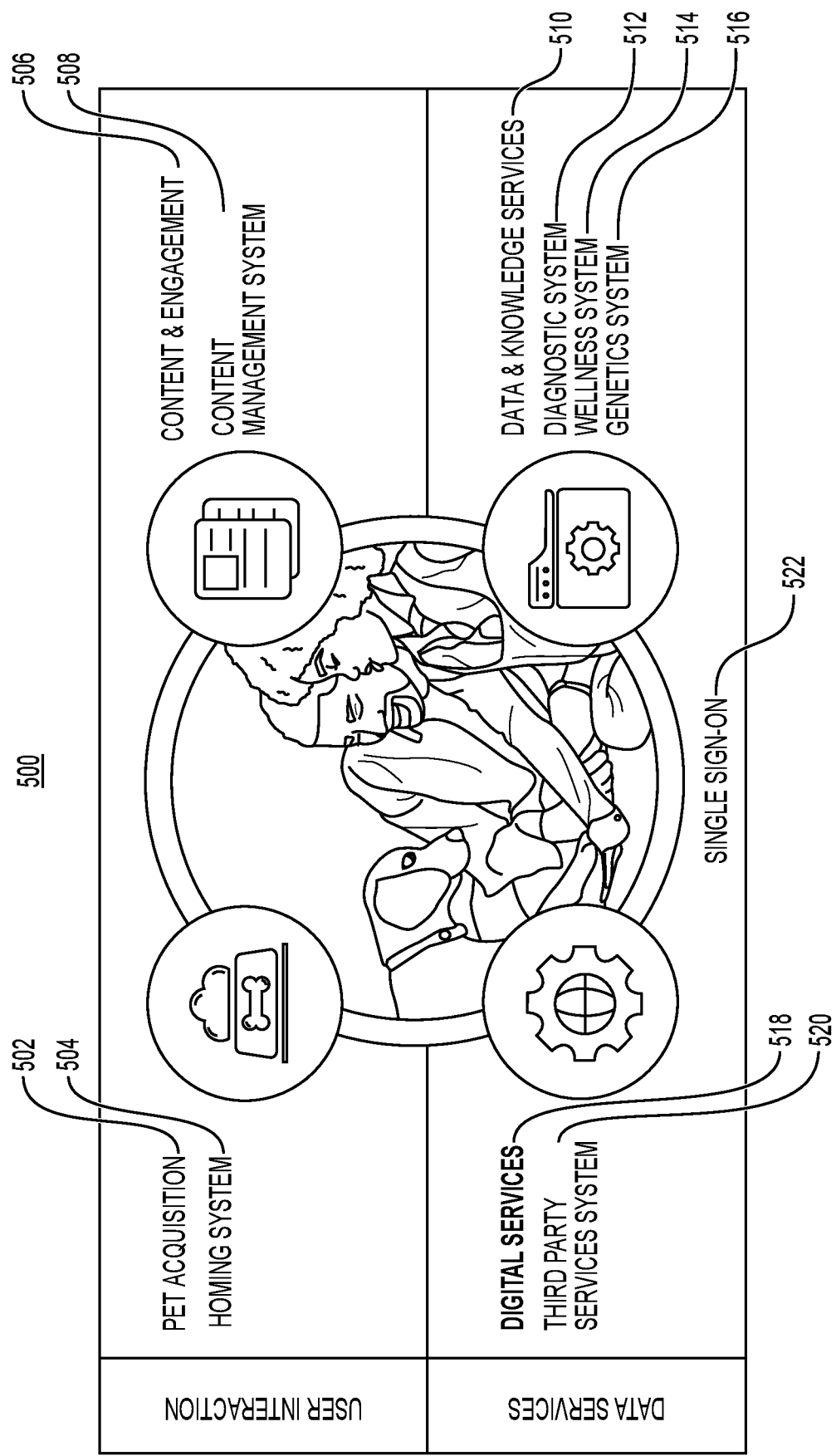
FIG. 5 depicts an exemplary platform flow, according to one or more embodiments.

FIG. 5 depicts an exemplary platform flow 500 that may be utilized with the techniques presented herein. Notably, the platform flow 500 may be performed by one or more processors of a server that is in communication with one or more user devices and other external system(s) via a network. However, it should be noted that platform flow 500 may be performed by any one or more of the server, one or more user devices, or other external systems.

The platform flow 500 may begin with a pet acquisition process 502, where the pet acquisition process 502 may utilize a homing system 504 (e.g., homing system 152). For example, the pet acquisition process 502 may utilize the homing system 504 in order to facilitate a user adopting and/or purchasing a pet.

After a user acquires the pet, the platform flow 500 may continue with providing content and engagement 506 to the user. For example, content and engagement 506 may utilize a content management system 508 (e.g., content management system 164) to provide personalized content (e.g., newsletters, advertisements) to the user.

The platform flow 500 may continue with providing data and knowledge services 510 to the user. For example, data and knowledge services 510 may utilize a diagnostic system 512 (e.g., diagnostic system 142), a wellness system 514 (e.g., wellness system 124), and/or a genetics system 516 (e.g., genetics system 170) to provide precision care to the user.

The platform flow 500 may continue with providing digital services 518 to the user. For example, digital services 518 may utilize a third party services system 520 (e.g., third party services system 182) to assist the user in searching for, and reserving, services for the user's pet.

In some embodiments, the user may be able to engage in all or some of the platform flow 500 by utilizing a single sign-on 522 (e.g., single sign-on 116). For example, the single sign-on 522 may allow for some or all of the user's activity in the platform flow 500 to be associated with the user and/or the user's pet.

Exemplary Environment

Figure 6:
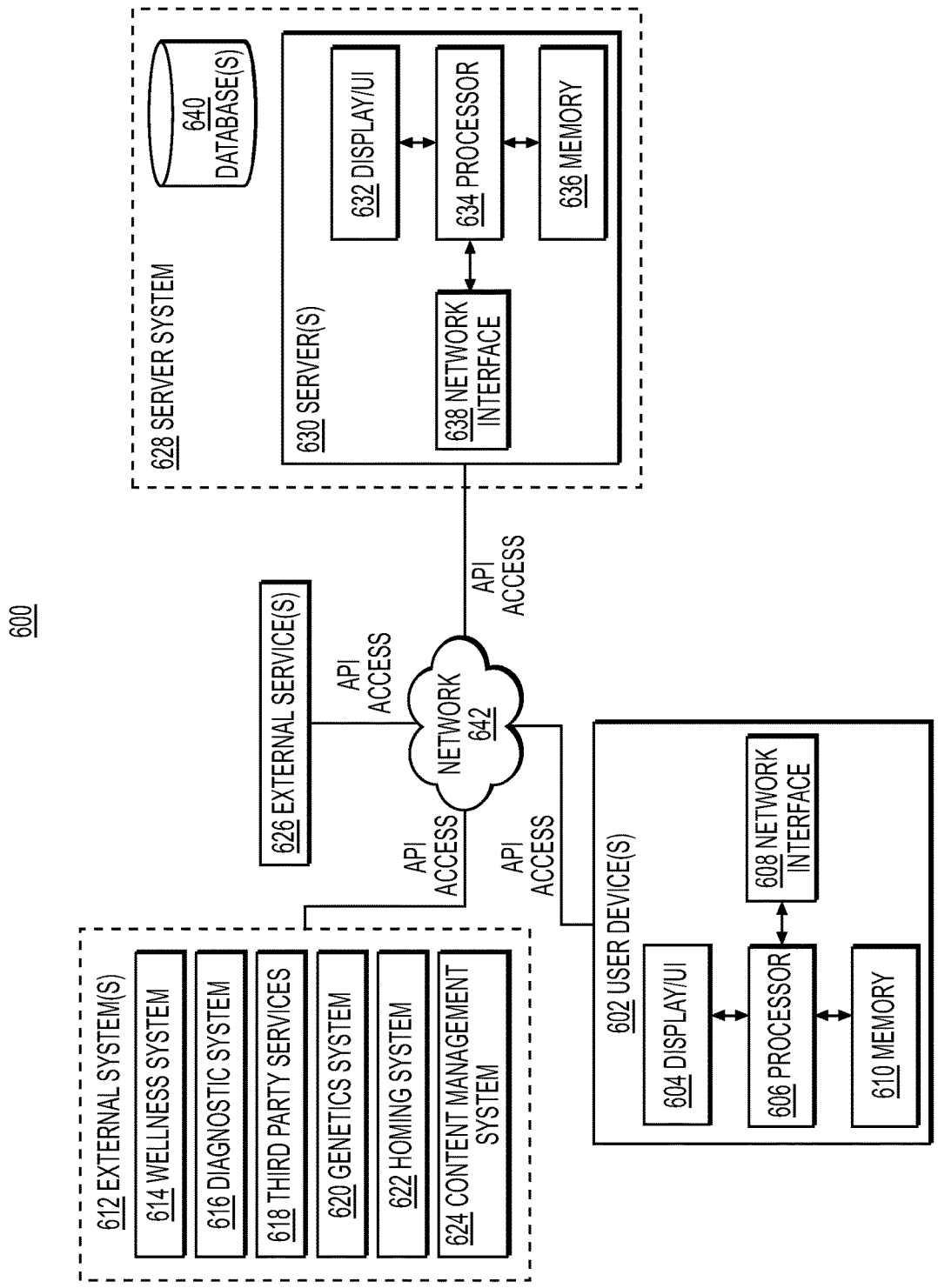
FIG. 6 depicts an exemplary environment that may be utilized with techniques presented herein, according to one or more embodiments.

FIG. 6 depicts an exemplary environment 600 that may be utilized with the techniques presented herein. One or more user device(s) 605, one or more external system(s) 626, and one or more server system(s) 628 may communicate across a network 642. As will be discussed in further detail below, one or more server system(s) 628 may communicate with one or more of the other components of the environment 600 across network 642. The one or more user device(s) 602 may be associated with a user, e.g., a user associated with at least one pet.

In some embodiments, the components of the environment 600 are associated with a common entity, e.g., a veterinarian, clinic, animal specialist, research center, or the like. In some embodiments, one or more of the components of the environment is associated with a different entity than another. The systems and devices of the environment 600 may communicate in any arrangement. As will be discussed herein, systems and/or devices of the environment 600 may communicate in order to receive, send, and/or store data.

The user device 602 may be configured to enable the user to access and/or interact with other systems in the environment 600. For example, the user device 602 may be a computer system such as, for example, a desktop computer, a mobile device, a tablet, etc. In some embodiments, the user device 602 may include one or more electronic application(s), e.g., a program, plugin, browser extension, etc., installed on a memory of the user device 602.

The user device 602 may include a display/user interface (UI) 604, a processor 606, a memory 610, and/or a network interface 608. The user device 602 may execute, by the processor 606, an operating system (O/S) and at least one electronic application (each stored in memory 610). The electronic application may be a desktop program, a browser program, a web client, or a mobile application program (which may also be a browser program in a mobile O/S), an applicant specific program, system control software, system monitoring software, software development tools, or the like. For example, environment 600 may extend information on a web client that may be accessed through a web browser. In some embodiments, the electronic application(s) may be associated with one or more of the other components in the environment 600. The application may manage the memory 610, such as a database, to transmit streaming data to network 642. The display/UI 604 may be a touch screen or a display with other input systems (e.g., mouse, keyboard, etc.) so that the user(s) may interact with the application and/or the O/S. The network interface 608 may be a TCP/IP network interface for, e.g., Ethernet or wireless communications with the network 642. The processor 606, while executing the application, may generate data and/or receive user inputs from the display/UI 604 and/or receive/transmit messages to the server system 628, and may further perform one or more operations prior to providing an output to the network 642.

External system(s) 612 may be, for example, one or more systems that collect, manage, and/or store data corresponding to one or more pets and/or one or more pet owners. The one or more external systems may include at least one of a wellness system 614, a diagnostic system 616, a third party services system 618, a genetics system 620, a homing system 622, and/or a content management system 624. External system(s) 612 may be in communication with other device(s) or system(s) in the environment 600 over the one or more networks 642. For example, external system(s) 612 may communicate with the server system 628 via API (application programming interface) access over the one or more networks 642, and also communicate with the user device(s) 602 via web browser access over the one or more networks 642.

External service(s) 626 may be, for example, one or more third party and/or auxiliary systems that integrate and/or communicate with the server system 628 in performing various document information extraction tasks. External service(s) 626 may be in communication with other device(s) or system(s) in the environment 600 over the one or more networks 642. For example, external service(s) 626 may communicate with the server system 628 via API access over the one or more networks 642, and also communicate with the user device(s) 602 via web browser access over the one or more networks 642.

In various embodiments, the network 642 may be a wide area network ("WAN"), a local area network ("LAN"), a personal area network ("PAN"), or the like. In some embodiments, network 642 may include the Internet, and information and data provided between various systems occurs online. "Online" may mean connecting to or accessing source data or information from a location remote from other devices or networks coupled to the Internet. Alternatively, "online" may refer to connecting or accessing a network (wired or wireless) via a mobile communications network or device. The Internet is a worldwide system of computer networks—a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

The server system 628 may include an electronic data system, e.g., a computer-readable memory such as a hard drive, flash drive, disk, etc. In some embodiments, the server system 628 includes and/or interacts with an application programming interface for exchanging data to other systems, e.g., one or more of the other components of the environment.

The server system 628 may include a database(s) 640 and server(s) 630. The server system 628 may be a computer, system of computers (e.g., rack server(s)), and/or or a cloud service computer system. The server system may store or have access to database(s) 640 (e.g., hosted on a third party server or in memory 638). The server(s) may include a display/UI 632, a processor 634, a memory 636, and/or a network interface 638. The display/UI 632 may be a touch screen or a display with other input systems (e.g., mouse, keyboard, etc.) for an operator of the server(s) 630 to control the functions of the server(s) 630. The server system 628 may execute, by the processor 634, an operating system (O/S) and at least one instance of a servlet program (each stored in memory 636).

Although depicted as separate components in FIG. 6, it should be understood that a component or portion of a component in the environment 600 may, in some embodiments, be integrated with or incorporated into one or more other components. For example, a portion of the display 632 may be integrated into the user device 602 or the like. In some embodiments, operations or aspects of one or more of the components discussed above may be distributed amongst one or more other components. Any suitable arrangement and/or integration of the various systems and devices of the environment 600 may be used.

In general, any process or operation discussed in this disclosure that is understood to be computer-implementable, such as the processes illustrated in FIGS. 3-4, may be performed by one or more processors of a computer system, such any of the systems or devices in the environment 600 of FIG. 6, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 6. One or more processors of a computer system may be included in a single computing device or distributed among a plurality of computing devices. A memory of the computer system may include the respective memory of each computing device of the plurality of computing devices.

Exemplary Device

Figure 7:
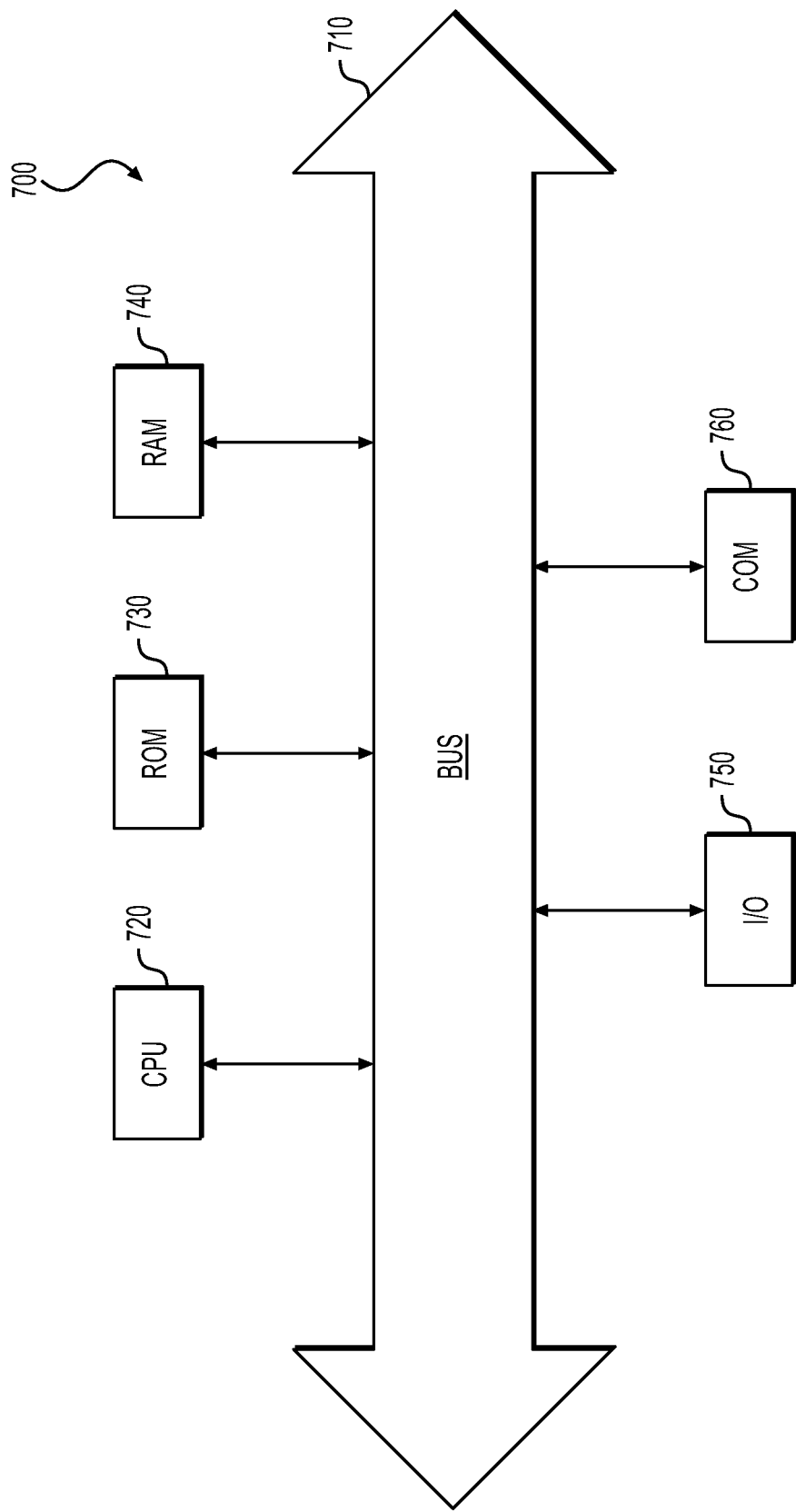
FIG. 7 depicts an example of a computing device that may execute the techniques described herein, according to one or more embodiments.

FIG. 7 is a simplified functional block diagram of a computer 700 that may be configured as a device for executing the environments and/or the methods of FIGS. 1-5, according to exemplary embodiments of the present disclosure. For example, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and also may include a secondary memory 730. Secondary memory 730, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include other similar means for allowing computer programs or other instructions to be loaded into device 700. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 700 also may include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

A computer system, such as a system or device implementing a process or operation in the examples above, may include one or more computing devices. One or more processors of a computer system may be included in a single computing device or distributed among a plurality of computing devices. A memory of the computer system may include the respective memory of each computing device of the plurality of computing devices.

A computer may be configured as a device for executing the exemplary embodiments of the present disclosure. For example, the computer may be configured according to exemplary embodiments of this disclosure. In various embodiments, any of the systems herein may be a computer including, for example, a data communication interface for packet data communication. The computer also may include a central processing unit ("CPU"), in the form of one or more processors, for executing program instructions. The computer may include an internal communication bus, and a storage unit (such as ROM, HDD, SDD, etc.) that may store data on a computer readable medium, although the computer may receive programming and data via network communications. The computer may also have a memory (such as RAM) storing instructions for executing techniques presented herein, although the instructions may be stored temporarily or permanently within other modules of computer (e.g., processor and/or computer readable medium). The computer also may include input and output ports and/or a display to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Furthermore, while some embodiments described herein include some but not other features included in other embodiments, combinations of features of different embodiments are meant to be within the scope of the invention, and form different embodiments, as would be understood by those skilled in the art.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for dynamically managing electronic transactions of petcare data, the method comprising:

hosting, by one or more processors, a user portal corresponding to at least one user and at least one pet, the user portal including at least one user profile that includes at least one user identifier and at least one pet profile that includes at least one pet identifier, wherein the at least one user profile includes the at least one pet identifier wherein the at least one pet profile includes microchip information corresponding to a microchip inserted into the at least one pet;

receiving, by the one or more processors, a first data set from a first external system, the first external system including at least one of: a wellness system, a diagnostic system, a homing system, or a genetics system, wherein the first data set includes the at least one user identifier, the at least one pet identifier, and pet activity data from at least one pet sensor, wherein the at least one pet sensor includes a smart pet litter box configured to track a use frequency and an activity type associated with the smart pet litter box;

in response to the receiving, calling, by the one or more processors, a content management component using an application programming interface (API) based on the first data set, wherein the content management system is configured to create personalized content based on communications with one or more external sources;

in response to the calling, receiving, by the one or more processors, a recommendation from the content management component, the recommendation based on the first data set that includes the pet activity data from the at least one pet sensor, wherein the recommendation includes a food recommendation, an activity recommendation, a product recommendation, a resource recommendation, or a third party service recommendation;

retrieving, by the one or more processors, at least one user database record corresponding to the at least one user identifier and at least one pet database record corresponding to the at least one pet identifier from one or more databases;

based on the receiving, updating, by the one or more processors, the at least one user database record and the at least one pet database record based on the first data set and the recommendation;

displaying, by the one or more processors, the recommendation on a user interface of the user portal;

receiving, by the one or more processors, user interaction feedback corresponding to the recommendation; and modifying, by the one or more processors, a future recommendation based on the user interaction feedback.

2. The computer-implemented method of claim 1, the method further comprising:

receiving, by the one or more processors, a second data set from a second external system, the second external system including at least one of: the wellness system, the diagnostic system, the homing system, the genetics system, or the third party services system, wherein the second data set includes the at least one user identifier and the at least one pet identifier;

in response to the receiving, calling, by the one or more processors, the content management component using the API based on the second data set;

in response to the calling, receiving, by the one or more processors, a second recommendation from the content management component, the second recommendation based on the second data set; and based on the receiving, updating, by the one or more processors, the at least one user database record at the at least one pet database record based on the second data set and the second recommendation.

3. The computer-implemented method of claim 2, the method further comprising:

displaying, by the one or more processors, at least one personalized advertisement on the user interface, the at least one personalized advertisement based on the first data set and/or the second data set.

4. The computer-implemented method of claim 2, wherein the second external system is the wellness system, and wherein the second data set includes activity data captured by a sensor worn by the at least one pet.

5. The computer-implemented method of claim 2, wherein the first external system or the second external system is the diagnostic system, and wherein the first data set or the second data set includes wellness plan data or diagnostic data corresponding to the at least one pet.

6. The computer-implemented method of claim 5, wherein the wellness plan data or the diagnostic data is based on the at least one pet profile.

7. The computer-implemented method of claim 2, wherein the first external system or the second external system is the homing system, and wherein the first data set or the second data set includes an adoption record, a registration record, or a personalized match based on the at least one user profile and/or the at least one pet profile.

8. The computer-implemented method of claim 2, wherein the first external system or the second external system is the genetics system, and wherein the first data set or the second data set includes a genetic data analysis.

9. The computer-implemented method of claim 2, wherein the first external system or the second external system is the third party services system, and wherein the first data set or the second data set includes booking data and/or a communication from an external service.

10. The computer-implemented method of claim 1, wherein the at least one user profile includes at least one of: a name, an address, a digital wallet, demographic data, an email address, payment history data, booking history data, or the at least one pet identifier.

11. The computer-implemented method of claim 1, the at least one pet profile including at least one of: a name, an image, a wellness score, at least one vaccination record, insurance policy data, medication history data, breed data, DNA data, wellness plan data, veterinarian history data, an adoption record, a registration record, booking history data, activity data, insurance information data, or pet savings account data.

12. A computer system for dynamically managing electronic transactions of petcare data, the computer system comprising:

at least one memory storing instructions; and at least one processor configured to execute the instructions to perform operations comprising:

hosting a user portal corresponding to at least one user and at least one pet, the user portal including at least one user profile that includes at least one user identifier and at least one pet profile that includes at least one pet identifier, wherein the at least one user profile includes the at least one pet identifier wherein the at least one pet profile includes microchip information corresponding to a microchip inserted into the at least one pet;

receiving a first data set from a first external system, the first external system including at least one of: a wellness system, a diagnostic system, a homing system, or a genetics system, wherein the first data set includes the at least one user identifier, the at least one pet identifier, and pet activity data from at least one pet sensor, wherein the at least one pet sensor includes a smart pet litter box configured to track a use frequency and an activity type associated with the smart pet litter box;

in response to the receiving, calling a content management component using an application programming interface (API) based on the first data set, wherein the content management system is configured to create personalized content based on communications with one or more external sources;

in response to the calling, receiving a recommendation from the content management component, the recommendation based on the first data set that includes the pet activity data from the at least one pet sensor, wherein the recommendation includes a food recommendation, an activity recommendation, a product recommendation, a resource recommendation, or a third party service recommendation;

retrieving at least one user database record corresponding to the at least one user identifier and at least one pet database record corresponding to the at least one pet identifier from one or more databases;

based on the receiving, updating the at least one user database record and the at least one pet database record based on the first data set and the recommendation;

displaying the recommendation on a user interface of the user portal;

receiving user interaction feedback corresponding to the recommendation; and modifying a future recommendation based on the user interaction feedback.

13. The computer system of claim 12, the operations further comprising:

receiving a second data set from a second external system, the second external system including at least one of: the wellness system, the diagnostic system, the homing system, the genetics system, or the third party services system, wherein the second data set includes the at least one user identifier and the at least one pet identifier;

in response to the receiving, calling the content management component using the API based on the second data set;

in response to the calling, receiving a second recommendation from the content management component, the second recommendation based on the second data set; and based on the receiving, updating the at least one user database record at the at least one pet database record based on the second data set and the second recommendation.

14. The computer system of claim 13, the operations further comprising:

displaying at least one personalized advertisement on the user interface, the at least one personalized advertisement based on the first data set and/or the second data set.

15. The computer system of claim 13, wherein the second external system is the wellness system, and wherein the second data set includes activity data captured by a sensor worn by the at least one pet.

16. The computer system of claim 13, wherein the first external system or the second external system is the diagnostic system, and wherein the first data set or the second data set includes wellness plan data or diagnostic data corresponding to the at least one pet.

17. The computer system of claim 16, wherein the wellness plan data or the diagnostic data is based on the at least one pet profile.

18. A non-transitory computer-readable medium storing instructions that, when executed by at least one processor, cause the at least one processor to perform operations for dynamically managing electronic transactions of petcare data, the operations comprising:

hosting a user portal corresponding to at least one user and at least one pet, the user portal including at least one user profile that includes at least one user identifier and at least one pet profile that includes at least one pet identifier, wherein the at least one user profile includes the at least one pet identifier wherein the at least one pet profile includes microchip information corresponding to a microchip inserted into the at least one pet;

receiving a first data set from a first external system, the first external system including at least one of: a wellness system, a diagnostic system, a homing system, or a genetics system, wherein the first data set includes the at least one user identifier, the at least one pet identifier, and pet activity data from at least one pet sensor, wherein the at least one pet sensor includes a smart pet litter box configured to track a use frequency and/or an activity type associated with the smart pet litter box;

in response to the receiving, calling a content management component using an application programming interface (API) based on the first data set, wherein the content management system is configured to create personalized content based on communications with one or more external sources;

in response to the calling, receiving a recommendation from the content management component, the recommendation based on the first data set that includes the pet activity data from the at least one pet sensor, wherein the recommendation includes a food recommendation, an activity recommendation, a product recommendation, a resource recommendation, or a third party service recommendation;

retrieving at least one user database record corresponding to the at least one user identifier and at least one pet database record corresponding to the at least one pet identifier from one or more databases;

based on the receiving, updating the at least one user database record and the at least one pet database record based on the first data set and the recommendation;

displaying the recommendation on a user interface of the user portal;

receiving user interaction feedback corresponding to the recommendation; and modifying a future recommendation based on the user interaction feedback.

19. The non-transitory computer-readable medium of claim 18, wherein the at least one user profile includes at least one of: a name, an address, a digital wallet, demographic data, an email address, payment history data, booking history data, or the at least one pet identifier.

20. The non-transitory computer-readable medium of claim 18, the at least one pet profile including at least one of: a name, an image, a wellness score, at least one vaccination record, insurance policy data, medication history data, breed data, DNA data, wellness plan data, veterinarian history data, an adoption record, a registration record, booking history data, activity data, insurance information data, or pet savings account data.

* * * * *